United States Patent [19]
Holtz

[11] Patent Number: 6,153,654
[45] Date of Patent: Nov. 28, 2000

[54] METHOD OF IMPROVING OUTCOME OF CARDIOPULMONARY BYPASS SURGERY

[76] Inventor: Russell R. Holtz, 3305 N. 18th St., Tacoma, Wash. 98406

[21] Appl. No.: 09/319,405

[22] PCT Filed: Dec. 4, 1997

[86] PCT No.: PCT/US97/22103

§ 371 Date: Jun. 4, 1999

§ 102(e) Date: Jun. 4, 1999

[87] PCT Pub. No.: WO98/24381

PCT Pub. Date: Jun. 11, 1998

Related U.S. Application Data

[60] Provisional application No. 60/032,522, Dec. 4, 1996.

[51] Int. Cl.[7] .................................................. A61K 31/135
[52] U.S. Cl. .................................................. 514/652
[58] Field of Search ............................................. 514/652

[56] References Cited

U.S. PATENT DOCUMENTS

| | | |
|---|---|---|
| 4,600,708 | 7/1986 | Reuter et al. . |
| 5,278,200 | 1/1994 | Coury et al. . |

OTHER PUBLICATIONS

Conti et al., Metabolic and Functional Effects of Carbohydrate Substrate with Single–Dose and Multiple–Dose Potassium Cardioplegia, *The Annals of Thoracic Surgery* 36:320–327 (1983).

Hammon et al., Perioperative Beta Blockade with Propranolol: Reduction in Myocardial Oxygen Demands and Incidence of Atrial and Ventricular Arrythmias, *The Annals of Thoracic Surgery* 38:363–367 (1984).

Mangano et al., Effect of Atenolol on Mortality and Cardiovascular Morbidity after Noncardiac Surgery, *The New England Journal of Medicine* 335:1713–1720 (1996).

Moffitt et al., Hemodynamics and Myocardial Metabolism after Acute β–Adrenergic Blockade in Coronary Patients, *Anesth. Analog.* 63:540–541 (1984).

Moffitt and Sethna, The Coronary Circulation and Myocardial Oxygenation in Coronary Artery Disease: Effects of Anesthesia, *Anesth. Analg.* 65:395–410 (1986).

Physician's Desk Reference, 46th Edition, 2459–2462 (1992).

Safwat et al., Use of Propranolol to Control Rate–Pressure Product During Cardiac Anesthesia, *Anesth. Analg.* 60:732–735 (1981).

Vickers, M.D., Adrenergic Drugs and their Antagonists in Anesthesia, *Brit. J. Anaesth.* 38:728–739 (1966).

*Primary Examiner*—Raymond Henley, III
*Attorney, Agent, or Firm*—Klarquist Sparkman Campbell Leigh & Whinston, LLP

[57] ABSTRACT

This invention concerns a method for improving the outcome of cardiac surgery in patients who undergo cardiopulmonary bypass on a heart-lung machine. More specifically, this invention concerns administration of therapeutic agents to improve objective measures of surgical outcome.

11 Claims, No Drawings

METHOD OF IMPROVING OUTCOME OF CARDIOPULMONARY BYPASS SURGERY

This application claim priority under 35 USC 119(e) other provisional application Ser. No. 60/032/522 filed Dec. 4, 1996 and is a 371 of PCT/US97/22103 filed Dec. 4, 1997.

FIELD OF THE INVENTION

This invention concerns a method for improving the outcome of cardiac surgery in patients who undergo cardiopulmonary bypass on a heart lung machine. More specifically, this invention concerns administration of therapeutic agents to improve objective measures of surgical outcome.

BACKGROUND OF THE INVENTION

Coronary artery bypass graft (CABG) surgery is an increasingly common treatment for ischemic heart disease. In this procedure, a reversed segment of the patient's own saphenous vein or internal mammary artery is anastomosed between the ascending aorta and one or more stenotic coronary arteries. The anastomosis allows blood from the aorta to bypass atherosclerotic occlusions in the coronary vessels that are producing myocardial ischemia and symptoms of angina.

CABG surgery is performed with the assistance of a heart-lung machine, which temporarily performs the gas exchange function of the lungs and the blood pumping function of the heart. Use of this machine in cardiac surgery is referred to as cardiopulmonary bypass (CPB), and it allows the heart to be arrested (using cardioplegia) during the surgery while blood is shunted through a venoarterial bypass circuit. This circuit performs extracorporeal oxygenation of the blood, and returns it to the arterial tree, bypassing the heart and the pulmonary circulation. CPB allows the surgeon to operate in a bloodless field on a motionless heart.

Although CABG surgery (and use of CPB) have substantially improved the therapeutic outcome of patients with advanced myocardial ischemia, this surgery still has several undesired consequences. Technetium pyrophosphate studies have shown that perioperative myocardial infarctions occur in 21–31% of all CABG patients. Even more highly sensitive Indium-111 monoclonal antibody scintigraphy has shown that perioperative myocardial damage was present in 82% of uncomplicated CABG surgeries. Such damage is particularly troublesome in patients who have unstable angina and already compromised myocardium, because this perioperative damage can further impair heart function.

Induction of anesthesia is complicated in patients with coronary artery disease (CAD) because inhalational anesthetic agents can induce hemodynamic swings in already myocardially compromised patients. Perioperative arrhythmias can complicate the postoperative recoveries of between 20% and 30% of patients following CABG surgery. Some of these events may be due to endogenous catecholamine release caused by the stress of surgery. Although beta adrenergic antagonists (such as propranolol) have long been known to block catecholamine mediated adrenergic responses, use of beta adrenergic antagonists in heart patients has long been viewed with caution. Traditional medical teaching has been that beta adrenergic antagonists are negative inotropes, which decrease the contractility of the heart muscle. Beta adrenergic antagonists (also known as beta blockers) have therefore been used cautiously in patients who have myocardial compromise.

High doses of beta adrenergic antagonists have been assiduously avoided intraoperatively in CABG patients prior to CPB, because conventional medical teaching has been that beta blockers will cause undesirable myocardial depression. Such myocardial depression has been considered particularly unwise in CPB because it has been thought to increase the difficulty of weaning a patient from CPB. Beta blockers have been thought to interfere with the pharmaceutical action of inotropic drugs, such as dopamine or epinephrine, that may be needed to wean a patient from the heart lung machine.

Yet another problem encountered after CABG surgery is neurological or neuropsychiatric compromise. About 2–6% of cardiac surgery patients sustain unequivocal neurologic injury (such as a frank stroke) in the perioperative period. As many as 30–60% of adult cardiac surgery patients experience more subtle neurologic abnormalities or neuropsychiatric changes. About 20–30% of patients still exhibit measurable decrements in neuropsychiatric performance six months postoperatively. These changes may be caused by platelet/fibrin thrombi, which can be directly observed in the retinal vasculature. These changes may also be a consequence of the hypercoagulable status of platelets often found in patients with coronary artery disease (CAD), and of the body's immune response to the CPB circuit. Neurological insult can also be caused by air microemboli or platelet thrombi that produce cerebral ischemia in the metabolically active tissue of the brain.

Another problem that has been observed with CPB is the initiation of an inflammatory response, apparently from the contact of blood with the CPB circuit. This response results in complement and platelet activation, with attendant formation of platelet-fibrin microemboli or platelet aggregation. These responses can produce tissue micro-ischemia, that results in ischemia and infarction in myocardial, cerebral, retinal or other types of tissue. The non-specific inflammatory nature of the CPB inflammatory response can also worsen patient outcome, and slow post-operative recovery.

It is accordingly an object of this invention to provide a method of performing CPB which reduces myocardial and other types of perioperative tissue ischemia and infarction.

Another object of the invention is to provide such a method that reduces tissue injury that may occur as a result of ischemia or infarction.

Yet another object of this invention is to provide an inexpensive and convenient intervention that can improve the outcome of patients undergoing CABG surgery, reduce postoperative morbidity, and minimize the cost of such surgery by decreasing the duration of intensive care unit and hospital stays.

SUMMARY OF THE INVENTION

The foregoing objects are achieved by a method of performing CABG surgery in which a therapeutically effective amount of a membrane stabilizing beta blocker such as propranolol is administered peri-operatively to a patient undergoing CPB, to reduce the effects of perioperative tissue ischemia. The propranolol is administered intravenously in a dose of at least 0.1 mg/kg, more particularly at least 0.2 mg/kg or even 1 mg/kg, and even more particularly a dose of 5–10 mg/kg, for example a dose of about 7 mg/kg, or greater. Doses of 50–700 mg propranolol, or greater, may be used in accordance with this method.

The beta blocker may be administered during the surgery, particularly after intubation for general anesthesia. The propranolol is administered, for example, as a continuous infusion or as multiple 0.5–1.0 mg boluses. In particular embodiments of the method, general anesthesia is achieved using a dose of the inhalational anesthetics enflurane or isoflurane sufficient to provide general anesthesia. A short acting narcotic, such as fentanyl (at a dose of about 30–40 mcg/kg) or sufentanil, may be administered intravenously to render the patient unconscious prior to intubation and administration of the inhalational agent. A muscle relaxant, such as the non-depolarizing agent vecuronium, may be administered in a dose of about 0.1 mg/kg prior to laryngoscopy and intubation. Particularly preferred embodiments of the invention maintain general anesthesia with enflurane at an inspired dose of, for example, 0.3 to 1.5% in oxygen.

DETAILED DESCRIPTION OF THE PREFERRED EMBODIMENTS

The present invention is a technique for use in cardiac anesthesia which improves cardiovascular stability, and measurably improves myocardial and neurological outcome. The method disclosed herein reliably eliminates undesired sympathetic adrenergic responses under anesthesia. The method also surprisingly provides myocardial and neurological protection to the patient without resulting in myocardial depression that the prior art taught would be expected with beta blockers.

The method of the present invention takes advantage of the surprising finding by the inventor that a beta blocker (such as propranolol) can be administered in large doses that protect the heart, brain and other organs from ischemic insult, without at the same time producing undesired or unacceptable myocardial depression. Normal intravenous dosing of propranolol in the prior art has been an initial dose of 0.03 mg/kg given at a rate of 0.5 mg/minute. In such previous treatments, doses are repeated every five minutes until desired hemodynamic responses are observed, or the total dose reaches 0.1 mg/kg.

The adverse effects of propranolol have been noted in the medical literature to be hypotension, airway constriction in patients with chronic obstructive pulmonary disease or reactive airway disease, and bradycardia. Marino, *The ICU Book,* Lea & Febiger, 1991 at page 287. One of the most prominent pharmacology texts teaches that propranolol decreases contractility of the heart, and causes generalized depression of myocardial function, which can cause death in large doses. Goodman & Gilman, *The Pharmacological Basis of Therapeutics,* Macmillan Publishing Company, 1985 at page 193.

This concern about myocardial depression from large doses of propranolol has long discouraged physicians from attempting to use doses of the drug greater than required to achieve beta adrenergic blockade. This concern has been particularly prominent with patients on CPB, whose already impaired myocardium has been considered especially vulnerable to a myocardial depressant. The use of large doses of beta blockers has been discouraged, particularly with patients undergoing CPB, because it was also thought that a large dose of beta blocker would complicate efforts to wean the patient from the heart lung machine. The present inventor has surprisingly found that propranolol does not cause the expected degree of myocardial depression and, in fact makes weaning from CPB easier, with decreased post-bypass inotropic and antiarrythmic requirements.

Membrane stabilizing doses of propranolol may be administered to the patient either during induction of anesthesia, during the surgery, or both. In preferred embodiments of the method, administration of the beta blocker in membrane stabilizing doses is performed after intubation of the patient, to help avoid episodes of asystole that sometimes occur with beta blockade during laryngoscopy. The propranolol may be given in 0.5 to 1 mg intravenous boluses administered at intervals of, for example, every few seconds, up to a total dose of 10 mg/kg (eg 700 mg in a 70 kg man), or even 20 mg/kg (eg 1400 mg in a 70 kg man).

This technique has been found to create a hypodynamic circulation which eliminates the effects of increased catecholamines on the myocardium, while also independently protecting ischemic or injured myocardium and reducing neurological impairment. The surprising superiority of this technique can be objectively demonstrated by numerous standard endpoints, such as fewer intraoperative and post-operative arrhythmias, shorter intensive care unit stays, lower post-operative creatinine kinase (CK) and myocardial isoenzyme (CKMB) levels, and shorter hospitalizations. Although the reason for these superior results are not fully understood, they appear to be attributable to membrane stabilizing and anti-oxidant properties of propranolol. These combined effects, which are seen at the high doses of the beta adrenergic antagonist drug used herein, appear to protect injured or ischemic myocardial and neurological tissue from being damaged by ischemic perioperative or intraoperative events. Propranolol has been found to be particularly effective because its antioxidant activity is not affected by the acidosis seen in ischemic tissue.

Another benefit of the high dose propranolol disclosed herein is improved tissue oxygenation. High-dose propranolol shifts the oxygen dissociation curve to the right, which improves oxygen delivery to the tissues.

A better understanding of the invention will be had by reference to the following specific examples.

EXAMPLE 1

A patient who is to undergo CABG surgery continues taking oral medications, such as antihypertensive and antianginal medications, up to and including the day of the surgery. On the day of surgery, the patient is premedicated with midazolam given i.m. or i.v., and then one or two large bore intravenous catheters are placed in veins. Further sedation is then given using intravenous midazolam, as needed. The patient is taken to the operating room and noninvasive monitors are applied (a seven channel EKG [I, II, III, AVR, AVL, AVF, V5], an automatic blood pressure cuff, and a pulse oximeter). Then invasive monitors are placed, including a radial arterial line and an internal jugular SvO2 Swan-Ganz catheter. These monitors are used to continuously determine the patient's hemodynamic indices during surgery.

The patient is pre-oxygenated, and anesthesia induced by administering sufficient intravenous fentanyl to induce anesthesia in the patient (usually 30–40 mcg/kg) then adding a non-depolarizing muscle relaxant (usually vecuronium in a dose of 0.1 mg/kg). Endotracheal intubation is then performed, and if hypotension is noted during induction, or during maintenance anesthesia, the hypotension is treated with small boluses or brief infusions of phenylephrine (usually 40–100 mcg boluses). When the patient is intubated and hemodynamically stable, post-induction hemodynamic indices are recorded. A continuous infusion of propranolol is then begun, or multiple ½ to 1 mg boluses of propranolol are administered. It is more convenient to use an infusion of propranolol, at a rate intended to administer the entire dose between the time of endotracheal intubation and placing the patient on CPB. The goal is to run the infusion or repeat the boluses for the duration of the surgery prior to cardiopulmonary bypass (CPB) to ensure continuous beta receptor blockade.

Propranolol in these doses is well tolerated in patients tested to date. The infusion is not discontinued when bradycardia occurs. When complete beta blockade has been established, additional propranolol (at least in the dose range described herein) appears to have no additive effects. If bradycardia becomes severe (under 40) or causes hemodynamic compromise, it could be treated with pancuronium or atropine or atrial pacing. If the surgeon is ready to initiate CPB prior to termination of the infusion, the remainder of the drug is given as a bolus. Should the infusion finish early, an additional bolus (for example at least 3 mg) may be given immediately prior to initiating CPB. This helps protect the heart from the deleterious effects of the catecholamine surge noted with CPB.

Unless the patient is tachycardic, acute beta-blockade is not provided immediately prior to induction, because such blockade could potentially result in asystole during laryngoscopy. In the inventor's experience with this technique, the narcotic induction alone, or if needed, a narcotic induction in combination with mask ventilation and titration of the inhalational anesthetic enflurane, can reliably blunt the sympathetic response to laryugoscopy. If the sympathetic response is not sufficiently blunted by these interventions, a small bolus (usually 1–2 mg.) of propranolol may be given.

Following induction, the inhalational anesthetic enflurane is used as the primary anesthetic agent, and titrated to achieve general anesthesia of a desired depth. If evidence of myocardial ischemia is noted during surgery (EKG changes, elevated intramyocardial pressures, etc.) an intravenous nitroglycerin infusion is titrated to relieve the evidence of ischemia. Also, because of the high incidence of myocardial ischemia noted on CPB, a nitroglycerin infusion is run at 200 mcg/min or higher if indicated until the aorta is cross-clamped. After the cross clamp is removed, the nitroglycerin infusion is resumed, then titrated or weaned as appropriate. The patient may then be weaned from CPB using a dopamine infusion (usually at 5 mcg/kg/min).

Beta blockade is useful to prevent the loss of myocardial energy stores due to the hyperdynamic response to catecholamines. The present inventor has found that propranolol given acutely prior to CPB, even in patients with severely impaired ventricular function, has surprisingly minimal effects on hemodynamic parameters. Additionally, the widespread concern that these patients will need greater hemodynamic support to be weaned from CPB has not been borne out by the data obtained by the applicant. Surprisingly, the exact opposite appears to be true. Patients who receive propranolol prior to CPB have required less, not more, inotropic support, even in patients who have severely impaired ventricular function.

Because CPB is associated with disseminated microemboli, all tissue, not just the heart is at risk from ischemia. Diffuse micro-ischemia is a likely explanation for neurobehavioral and neuropsychiatric changes seen in a majority of CABG patients after bypass surgery. Cellular communication is a membrane mediated phenomenon. Therefore, learning, memory, sensation, and movement are all dependent upon intact, functioning neuronal cell membranes. The present inventor has found that propranolol's lipophilicity apparently allows its protective antioxidant and membrane stabilizing effects to be exerted in all tissues, especially the brain, as well as the liver, kidneys, and other organs.

The safest maximum tissue protection by propranolol is believed to be at doses between 5 and 10 mg/kg, or even as high as 20 mg/kg. Extremely high doses (for example in excess of 30/mg/kg) may exhibit negative results, and possibly interfere with calcium metabolism and sodium- potassium gates in cell membranes. In a 70 kg man, for example, an intravenous dose of propranolol of 700 mg may be administered, which is much higher than previous therapeutic doses of propranolol.

Acute intravenous beta blockade with propranolol, in accordance with the present invention, may also be useful in patients who are taking oral propranolol preoperatively. High oral doses are well tolerated and build tissue levels of the drug. But, beta receptor blockade may not be ensured unless propranolol is given intraoperatively. Also acute increases in tissue levels are believed to be efficacious in the present method because the body continuously eliminates the drug.

Other drugs having beta adrenergic antagonist activity and antioxidant activity may also be used to reduce ischemic tissue injury. An example of such a drug is carvedilol, which is a combined alpha/beta blocker.

EXAMPLE 2

This example provides statistical evidence that treatment of patients undergoing CPB with high dose propranolol shortens recovery time and improves objective indicators of surgical outcome. Seventy-two consecutive patients received propranolol (Group 1), at least 3 mg i.v., up to 0.1 mg/kg, while undergoing coronary artery surgery. These patients were compared with 72 randomly selected CABG surgery patients (Group 2) who did not receive pre-bypass propranolol membrane stabilization during the same period of time. The patients were treated in accordance with the method described in detail in Example 1. General anesthesia in these patients was performed with an intravenous dose of either fentanyl or sufentanil with a muscle relaxant (vecuroniuni), supplemented by an inhalational anesthetic (usually enflurane, otherwise isoflurane) inspired in oxygen.

A comparison was made between the two groups of the overall incidence of postoperative supraventricular and ventricular arrhythmias, inotropic and antiarrhythmic drug use, and length of stay in the intensive care unit and hospital. Patients in each group were also compared according to their preoperative ejection fraction (EF): EF>55%, EF=35–54%, and EF<35%.

Patients in Group 1 and all Group 1 EF subsets experienced clinically fewer arrhythmias, less drug intervention, shorter ICU admission, and shorter overall hospitalization. A p value <0.05 was deemed significant. Statistical significance was achieved for an overall shorter hospitalization for Group 1 overall (−1.70 days +/−0.90 SEM, p=0.06) and a four day shorter ICU stay in the Group 1 EF<35% subgroup (p=0.07).

The following Table 1 summarizes some of the improved results obtained with the present invention at 0.2–0.5 mg/kg. In this Table, LOS is an abbreviation for Length of Stay in the hospital, LOS ICU is an abbreviation for Length of Stay in the Intensive Care Unit. CPK stands for creatinine phospholinase (an enzyme released in response to muscle injury), and CPK MB is an abbreviation for creatinine phosphokinase MB (an enzyme specifically released from myocardium after episodes of myocardial ischemia).

TABLE 1

|  | Propranolol | N | Control | N | P Value |
|---|---|---|---|---|---|
| Mean LOS | 5.5 | 13 | 6.0 | 189 | 0.031 |
| Mean LOS Proc:36.15 | 5.5 | 13 | 6.8 | 70 | 0.005 |
| Mean LOS ICU | 1.86 | 15 | 2.34 | 137 | 0.038 |
| Mean LOS PCU | 2.40 | 10 | 3.00 | 57 | 0.001 |
| CPK MB | 35.33 | 15 | 65.86 | 137 | 0.005 |
| CPK | 717.06 | 15 | 957 | 137 | 0.026 |
| Packed RBC Units | 1.26 | 15 | 1.97 | 136 | 0.007 |
| Atrial Fibrillation | 13.3% | 15 | 37.78% | 90 | 0.065 |

LOS = length of stay
CPK = creatinine phosphokinase

The data in Table 1 demonstrate that mean length of stay in the ICU and the hospital were reduced in patients who were treated in accordance with the method of the present invention. Markers of muscle injury (CK), and particularly myocardial muscle injury (CPK MB) were also reduced in patients treated in accordance with the invention, as compared to controls. Post-operative atrial fibrillation was also reduced in patients who were treated with high dose propranolol in accordance with the present invention.

Administering high doses of propranolol to patients prior to CPB contravenes long accepted medical teaching that beta adrenergic blockade of patients, especially those with myocardial dysfunction, must be avoided. Conventional medical theory has long been that high doses of beta adrenergic blockers (such as propranolol) will induce heart failure in patients with already compromised myocardium. The present invention has required a disregard of that teaching, and has surprisingly found that high doses of membrane stabilizing beta adrenergic antagonists (such as propranolol) can improve the outcome of patients undergoing CPB. This class of drugs also provides antioxidant activity that interrupts free radical reactions involved in permanent tissue damage, reduces catecholamine-induced myocardial stress, and helps avoid thrombotic events that lead to tissue ischemia and death.

EXAMPLE 3

The following Tables provide blood levels of creatinine kinase (CK) and its myocardial isoenzyme (CKMB) for patients who were treated with 1 mg/kg of propranolol intraoperatively during CABG surgery (Table 2) and patients who were not treated with propranolol in accordance with the method of this invention (Table 3). The mean CK in the population treated with propranolol was 663 instead of 848 (control), while the CKMB was 38.3 instead of 57.7 (control). The lower values in the propranolol treated subjects is an indication that they had less tissue ischemia than the subjects who did not receive the tissue protective doses of propranolol.

TABLE 2

CK and CKMB in Subjects Given 1 mg/kg Propranolol

| Subject | CK | CKMB |
|---|---|---|
| 1 | 659 | 57.0 |
| 2 | 1097 | 68.5 |
| 3 | 582 | 67.9 |
| 4 | 248 | 11.9 |
| 5 | 581 | 33.5 |
| 6 | 410 | 13.5 |
| 7 | 949 | 147.7 |
| 8 | 646 | 47 |
| 9 | 355 | 22.8 |
| 10 | 2688 | 73.2 |
| 11 | 430 | 27.4 |
| 12 | 427 | 15.7 |
| 13 | 633 | 49.4 |
| 14 | 442 | 24.9 |
| 15 | 174 | 14.8 |
| 16 | 347 | 16.4 |
| 17 | 175 | 19.3 |
| 18 | 601 | 49.4 |
| 19 | 1712 | 25.0 |
| 20 | 330 | 16.7 |
| 21 | 433 | 21.0 |
| 22 | 668 | 37.9 |
| TOTAL | 14585 | 843.9 |
| MEAN | 663 | 38.3 |

TABLE 3

CK and CKMB in Subjects Not Given Propranolol

| Subject | CK | CKMB |
|---|---|---|
| 1 | 649 | 47.2 |
| 2 | 753 | 57.5 |
| 3 | 732 | 39.6 |
| 4 | 437 | 20.0 |
| 5 | 413 | 52.4 |
| 6 | 979 | 103.5 |
| 7 | 761 | 91.0 |
| 8 | 355 | 15.0 |
| 9 | 2463 | 332.4 |
| 10 | 942 | 13.5 |
| 11 | 543 | 79.3 |
| 12 | 347 | 50.7 |
| 13 | 582 | 45.8 |
| 14 | 1450 | 55.4 |
| 15 | 668 | 30.2 |
| 16 | 498 | 24.7 |
| 17 | 3526 | 41.2 |
| 18 | 990 | 31.5 |
| 19 | 428 | 31.3 |
| 20 | 444 | 26.8 |
| 21 | 471 | 10.5 |
| 22 | 674 | 70.7 |
| TOTAL | 18656 | 1271 |
| MEAN | 848 | 57.7 |

EXAMPLE 4

The microemboli that are often observed during CPB surgery are believed to be a result of the inflammatory reaction that occurs with blood contacting the (foreign) CPB circuit. The production of microemboli is reduced, but not eliminated, by heparin coated circuits. The "circuit" refers to and includes the tubing and other components through which blood is removed from and returned to the patient. The Carmeda circuit manufactured by Medtronic Bio-Medicus of Eden Prairie, MN 55344 is an example of a currently available heparin coated circuit that may reduce microemboli production. An example of such a circuit is shown in U.S. Patent No. 5,278,200 which is incorporated by reference. The combination of the anesthetic technique of the present invention with the heparin coated circuit could substantially reduce mortality and morbidity associated with open heart surgery.

Heparin is a complex carbohydrate known as mucopolysaccharide or glycosaminoglycan used to prevent formation of clots. However, heparin coating may allow platelet adhesion and may increase bleeding at surgical sites. Examples of the immobilization of heparin or heparin analogues on polymeric surfaces are described in Kim & Feijen, Crit. Rev. Biocompatibility 1(3):229 (1985) and Jozefowicz & lozefowicz J. Am. Soc. Art. Intem. Org. 8:218 (1985). Methods of making biocompatible heparin-like coatings on polymeric substrates (such as polyurethane), or blending them into substrates, are shown in U.S. Pat. No. 5,278,200 which is incorporated by reference. This patent discloses biocompatible coatings made by co-polymerization of acrylic acid and 2-acrylamido-2-methyl propane sulfonic acid.

A complete heparin coating of the CPB circuits reduces the body's inflammatory response to the surfaces in the heart lung machine that contacts blood. However the heparin coating of the circuit is incomplete and/or is dislodged during use. Heparin is a large nonhomogeneous molecule that may be a poor substrate to coat the CPB circuits. Heparin is basically a polymer of glucose molecules, which is large and extremely nonhomogeneous (a molecular weight of 12,000 to 17,000 with some molecules being much larger). These large molecules can impede transfer of oxygen and the passage of cells through the oxygenator during CPB. They can disturb laminar flow and exposes the coating to shear forces that can disrupt covalently bonded tethers between the heparin and circuit wall.

The present inventor proposes that a smaller more homogenous molecule can be used to make blood contacting surfaces in the heart lung machine more biocompatible. Such a molecule would, for example, be glucose itself itself, or the altered glucose molecule that is polymerized to make hetastarch, found in Hespan, available from Du Pont Pharmaceuticals of Wilmington, DE. Hetastarch is an artificial colloid derived from a waxy starch composed almost entirely of aniylopectin. Hydroxyethyl ether groups are introduced into the glucose units of the starch to yield a product with a molecular weight of approximately 480,000 with a range of 400,000 to 550,000. This material is described in U.S. Pat. No. 4,803,102, which is incorporated by reference.

Alternative coatings include a sulfonated glucose-like moiety. A sulfonated glucose molecule with a hydroxyethyl ether or similar attachment will provide a smooth noninflammatory surface at least four times thinner than the heparin model.

This thinner internal coating will substantially improve the efficiency of the oxygenator, and reduce shearing forces between the internal wall and blood in the circuit.

Other potential coatings include a modified thin lipid or an amino acid layer. Any of these materials could be attached to or blended into a polymeric material, such as tubing of a CPB circuit, in the manner described in U.S. Pat. No. 5,278,200.

Having illustrated and described the principles of the invention in several preferred embodiments, it should be apparent to those skilled in the art that the invention can be modified in arrangement and detail without departing from such principles. I claim all modifications coming within the spirit and scope of the following claims, including equivalents thereof.

I claim:

1. A method of improving outcome of a subject undergoing cardiopulmonary bypass surgery, comprising the step of peri-operatively administering to the subject a therapeutically effective amount of an intravenous beta adrenergic antagonist that inhibits tissue damage from ischeniia.

2. The method of claim 1 wherein the beta adrenergic antagonist is propranolol, and the propranolol is administered intravenously in a dose of at least 0.1 mg/kg.

3. The method of claim 2 wherein the propranolol is administered in a dose of at least 1 mg/kg.

4. The method of claim 3 wherein the propranolol is administered in a dose of 5–8 mg/kg.

5. The method of claim 4 wherein the propranolol is administered in a continuous intravenous infusion.

6. The method of claim 2, wherein the propranolol is administered in a plurality of intravenous boluses of about 0.5–1 mg/kg.

7. The method of claim 1, wherein the beta adrenergic antagonist is administered after intubation, but before placing the subject on cardiopulmonary bypass.

8. The method of claim 1, further comprising the step of administering enflurane inhalational anesthetic to the subject.

9. The method of claim 8, further comprising inducing anesthesia with a narcotic.

10. A method of improving outcome of CABG surgery in patients undergoing cardiopulmonary bypass, comprising the steps of:

inducing unconsciousness in a patient by administering an anesthetically effective intravenous dose of a narcotic;

providing general anesthesia with an anesthetically effective dose of enflurane;

administering a dose of about 5–10 mg/kg propranolol to the patient undergoing coronary artery bypass graft surgery after the patient is intubated but before initiating cardiopulmonary bypass; and then initiating cardiopulmonary bypass.

11. The method of claim 10, further comprising performing cardiopulmonary bypass on a heart lung machine having tubing with an internal coating of non-inflammatory or non-reactive material.

\* \* \* \* \*

UNITED STATES PATENT AND TRADEMARK OFFICE
CERTIFICATE OF CORRECTION

PATENT NO. : 6,153,654
DATED : November 28, 2000
INVENTOR(S) : Russell R. Holtz

It is certified that error appears in the above-identified patent and that said Letters Patent is hereby corrected as shown below:

Column 6,
Lines 63-64, "phospholinase" should read -- phosphokinase --.

Column 7,
Line 44, "isocnyzyme" should read -- isoenzyme --.

Column 9,
Line 8, "lozefowicz" should read -- Jozefowicz --.
Line 38, "aniyolpectin" should read -- amylopectin --.

Column 10,
Line 16, "ischeniia" should read -- ischemia --.

Signed and Sealed this

Twenty-ninth Day of January, 2002

*Attest:*

JAMES E. ROGAN
*Attesting Officer*    Director of the United States Patent and Trademark Office